United States Patent [19]

Matskevich et al.

[11] 4,092,843
[45] June 6, 1978

[54] APPARATUS FOR TESTING THE READINESS OF HEAT-TREATED COAL FOR MOULDING

[76] Inventors: Danil Danilovich Matskevich, prospekt Gagarina, 6 mikroraion, 15, kv. 88; Nina Efimovna Ivashkova, ulitsa Sharikovaya, 51, kv. 2; Viktor Vasilievich Gavrikov, ulitsa Otakara Yarosha, 15, kv. 49, all of Kharkov, U.S.S.R.

[21] Appl. No.: 816,944

[22] Filed: July 19, 1977

[51] Int. Cl.² ............................................. G01N 3/00
[52] U.S. Cl. .................................. 73/17 R; 73/88 R
[58] Field of Search ................. 73/17 R, 88 R, 87, 94

[56] References Cited

PUBLICATIONS

"Plastic Properties of Coal by the Constant-Torque Gieseler Plastometer", ASTM, 9/24/71.

Primary Examiner—Anthony V. Ciarlante
Attorney, Agent, or Firm—Fleit & Jacobson

[57] ABSTRACT

An apparatus for testing the readiness of heat-treated coal for moulding, said readiness being evaluated in terms of time as a span between the moment of exerting pressure on a test sample of heated coal and that of the beginning of the coal swelling, has a receptacle for accommodating a test sample taken from a stream of coal, and a plunger associated therewith. The receptacle comprises a sleeve open at both ends which is secured to a bracket fixed on a vertical shaft rotatable by a drive means provided therefore. The part of the shaft which carries the bracket is placed within a casing which has a coal feed pipe on its top and a coal disposal pipe on its slant bottom. The coal feed pipe is located at a point just over the path of the receptacle rotation. Inside the casing along the path of rotation of the receptacle with the plunger, there are provided a first guide member positioned at the level of the top end face of the receptacle so as to close the entrance passage thereof on the respective part of the path of rotation, and a second guide member positioned under said first guide member, suitably pivoted and connected through a lever system with a weight which is adapted to urge this second guide member towards said first guide member, whereby the coal sample in the receptacle is compressed between the plunger and the first guide member.

4 Claims, 11 Drawing Figures

APPARATUS FOR TESTING THE READINESS OF HEAT-TREATED COAL FOR MOULDING

The present invention relates to control means used in heat treatment of coals, and more particularly to apparatus for testing the readiness of heat-treated coal for moulding.

The invention can be most advantageously used in the production of moulded blast-furnace coke from gas coals and medium-sintering coals.

There is known in the prior art a device for testing the readiness of heat-treated coal for moulding, which is determined in terms of time as a span between the moment of exerting pressure on a sample of heated coal and the beginning of the coal swelling (cf. USSR Inventor's Certificate No. 370,225), comprising a receptacle for accommodating a coal sample taken from a coal stream, which receptacle is placed in a conduit wherein said coal stream flows, a shutter mounted in said coal conduit and used to direct the coal stream into the receptacle, which shutter is controllable manually from outside, a plunger adapted to enter said receptacle, for which purpose the receptacle filled with coal is moved towards the plunger and manually fixed in position relative to said conduit, means for driving said plunger within said receptacle to compress the coal sample in the form of a hand-operated hydraulic drive, and a means for indicating the beginning of the plunger displacement within the receptacle caused by the coal-sample swelling, which indicating means comprise a pointer connected through a lever system with the plunger. The initial movement of said pointer caused by the plunger motion to compress the test sample and by its displacement as the coal-sample starts swelling are observed visually, and the span of time between these moments is measured by means of a hand-operated timer.

This device operates as follows.

A stream of heated coal continuously flows along the bottom of the inclined conduit, wherein said shutter is mounted. To take a coal sample, the receptacle, which is provided with an opening along some part of its length and fixed on a rod, is driven by pushing this rod into the conduit so that the opening becomes positionally coincident with the shutter. The latter is then turned by hand, whereby the stream of coal is directed into the receptacle opening. After the receptacle has been filled with coal, the shutter is turned back to its initial position. Thereafter, the rod is acted upon to put the receptacle on the plunger so that the opening on the receptacle is closed by the plunger and the test sample is moved to the part of the receptacle adjoining the rod. The rod with the receptacle is then fixed in this position by turning a respective control lever.

The hydraulic drive is then actuated by hand through directing a working fluid thereinto, whereby the plunger moves and applies pressure to the coal sample, simultaneously imparting motion to the indicating pointer. Upon observation of the pointer movement, the hand-operated timer is actuated. After a time interval depending on the temperature and method of heating, the heated coal being under pressure in the receptacle begins to swell owing to thermochemical processes taking place therein, accompanied by the accumulation of gaseous desintegration products. The swelling causes displacement of the plunger in a direction opposite to that of its pressure movement. The beginning of this displacement, which is imparted to the pointer, is observed and at this moment the timer is stopped. The timer reading makes up an attribute which characterizes the readiness of the heat-treated coal for moulding.

Manual control of the device and visual observation of the reference points during operation introduce observation and indication errors in the measuring results. In addition, the shutter, the receptacle, and the plunger with the indicator are actuated with the aid of intermediate links which are reciprocatingly movable through the conduit walls, being provided with sealing means. Movement of these links from a relatively cool outside environment into a hot atmosphere inside the conduit and back is accompanied with condensation and deposition thereon of condensed volatile substances emitted by heated coal. These sediments increase resistance to the motion of the links through the seals and cause damage thereto.

As a result, known devices cannot ensure maintained accuracy of testing the readiness of heat-treated coal for moulding, they should be stopped fairly often for cleaning from the above-mentioned sediments, which makes servicing thereof cumbersome. The impairement of seals results in greater physical efforts needed to operate the device, which deteriorates labour conditions.

It is, therefore, an object of the present invention to provide an apparatus for testing the readiness of heat-treated coal for moulding, which ensures higher accuracy of testing therewith and facilitates servicing thereof.

Another object of the invention is to provide an apparatus for testing the readiness of heat-treated coal for moulding which operates automatically.

The invention essentially resides in an apparatus for testing the readiness of heat-treated coal for moulding, assessed in terms of time as a span between the moment of exerting pressure on a sample of heated coal and the beginning of the coal swelling, comprising a receptacle for accommodating a test sample taken from a coal stream, a plunger, means for driving said plunger within said receptacle to compress said coal sample, and a means for indicating the beginning of the plunger displacement caused by the coal swelling, wherein, according to the invention, said receptacle is formed of a sleeve open at both ends and vertically mounted on a bracket fixed to a vertical shaft provided with a drive for its rotation, a part of the shaft which carries the bracket with the sleeve and the plunger being placed in a closed casing having on its top a feed pipe for letting therein the coal stream, which pipe is positioned over the path of rotation of the receptacle with said shaft, and a slant bottom with a disposal pipe for removing the coal therefrom, said means for driving the plunger within the receptacle to compress the coal sample includes a first guide member positioned inside the casing in a horizontal plane along the path of rotation of the receptacle with the plunger at the level of the receptacle top end face so that said first guide member closes the entrance passage of the receptacle, a second guide member positioned inside the casing under the first guide member along the same part of the receptacle path of rotation, said second guide member being connected through a lever system with a weight with urge it towards the first guide member, and having a profile with an ascending and horizontal parts thereof arranged in series and used for interaction with the lower end of the plunger as it rotates with the receptacle, whereby the coal sample is compressed between the plunger and said first guide member, said second guide member being also connected through said lever system with said means for indicating the beginning of its displacement together with the plunger caused by the test coal swelling, a third and a fourth guide members which are fixedly positioned in series within the casing along the subsequent portion of the receptacle path of rotation, said third and fourth guide members having, respectively, an ascending and descending profiles which are used to act on the plunger for a further upward movement of the plunger within the receptacle to remove the coal sample therefrom, and for the subsequent lowering of the plunger to its initial position, means for stopping the drive of rotation when the receptacle comes to a position preceding the point where the path of its rotation intersects the stream of coal, and to a position on the horizontal part of the second guide member, and means for starting the drive of rotation as the coal sample begins swelling.

The aforesaid features of the present invention allow all the operations, namely, the taking of a sample of heated coal into the receptacle, the exertion of a given pressure thereon, the keeping of the coal under the pressure until it begins to swell, the subsequent removal of the coal from the receptacle, the bringing of all the components of the apparatus into their initial positions, i.e. the entire operational cycle, to be carried out automatically and operated by remote control, e.g. from a central control station of an installation wherein the apparatus according to the present invention is used. Here, the testing results can be registered by means of an electic timer. That makes it possible to reduce the personnel attending to the installation wherein the apparatus is incorporated, and to provide for improved process quality control.

Furthermore, in an apparatus according to the invention there are no elements moving into the apparatus casing from outside, and all links between the components placed interiorly and exteriorly of the casing are accomplished through rotary elements mounted with the use of seals, which excludes carbonic resinous deposits of these elements and thereby provides for accurate testing and reliable operation thereof over a long period of time and also facilitates servicing and maintenance of the apparatus.

It is desirable that said means for indicating the beginning of the plunger displacement due to coal swelling should comprise a primary element connected to said lever system, a secondary element adapted to be in engagement with said primary element and connected with a means for disengaging said secondary element from said primary element upon a signal generated by said means for stopping said drive when the receptacle with the plunger comes onto the horizontal part of the profile of said second guide member, and a sensor used to generate a signal indicative of the beginning of the coal swelling when said primary element is displaced relative to said secondary element.

This arrangement provides for selective operation of the sensor responsive to coal swelling, which operates only during the downward movement of the plunger with the second guide member caused by the swelling of the coal sample and does not respond to other displacements thereof, e.g. those caused by increased resistance to the compression of the coal sample in the receptacle due to inadequate heat treatment of the coal.

That results in higher accuracy of coal readiness testing and excludes malfunctions of the apparatus.

It is expedient that a safety clutch should be introduced in the drive for rotation of said shaft, which slips when the receptacle and the plunger become jammed between the first and second guide members while compressing a sample of inadequately heat-treated coal, and the first guide member should be adapted to shift upwards under the action of the receptacle top end face and should be provided with a controllable locking means for fixing said first guide member in alignment with said top end face of the receptacle.

That prevents damage to the apparatus when poorly heat-treated coal is erroneously fed thereinto, allows said apparatus to be freed from the defective coal sample and to be prepared for the next working cycle by the withdrawal of said locking means from the first guide member, which can be done by conventional means operated by remote control.

All these features of the invention make for further increase in operational reliability of the apparatus, which is thereby provided with protection from clumsy handling.

A preferred embodiment of the invention will now be described in detail by way of example with reference to the accompanying drawings, wherein.

Figure 1:
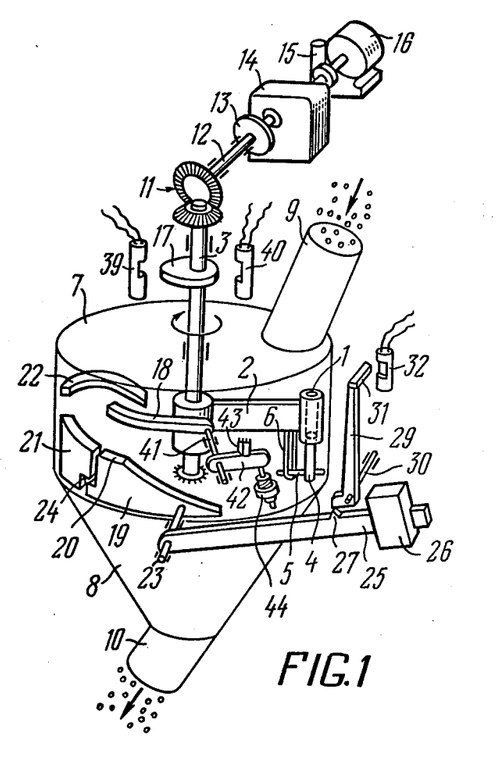
FIG. 1 is a schematic view of an apparatus for testing the readiness of heat-treated coal for moulding according to the invention, with a means for indicating the beginning of the plunger displacement caused by the coal-sample swelling.

Referring now to FIG. 1 of the drawings, an apparatus according to the present invention has a receptacle 1 which is a hollow cylindrical sleeve open at both ends. The sleeve is vertically fixed to a bracket 2 which is rigidly mounted on a vertical shaft 3.

A plunger 4 is slidably mounted in the receptacle 1 so that it is capable of axial movement therein. The travel of the plunger 4 within the receptacle 1 is limited by a pin 5 which is fixed crosswise on the lower end of the plunger 4. The pin 5 bears up against the bottom end face of the receptacle 1 when the plunger 4 is in its up-permost position, and against a yoke 6 attached to the bracket 2 when the plunger is in its lowermost position.

A part of the shaft 3 which carries the bracket 2 with the receptacle 1 and the plunger 4 is placed in a casing 7 which has a slant bottom 8 (funnel-like, as shown in FIG. 1, or flat).

A feed pipe 9 for letting a stream of coal in the casing 7 is fixedly mounted on the top thereof just over the path of rotation of the receptacle 1 with the shaft 3, and a discharge pipe 10 for coal removal is fixed to the bottom 8 of the casing 7.

The end of the shaft 3 that extends outside the casing 7 carries a driven gear of a bevel gearing 11 which is in mesh with a driving gear thereof mounted on a horizontal shaft 12. The latter is connected through a safety clutch 13 to an output shaft of a reduction gear unit 14, an input shaft thereof being connected through a coupling with a brake 15 to an electric motor 16.

A control element 17, e.g. a disc cam, is fixedly mounted on the shaft 3 outside the casing 7.

Inside the casing 7 along the path of rotation of the receptacle 1 there is placed a first guide member 18, which is spaced from the axis of the shaft 3 a distance equal to that between the axes of the shaft 3 and the receptacle 1. This guide member 18 is positioned in a horizontal plane at the level of the top end face of the receptacle 1. positioned under the first guide member 18 is second guide member 19 which has an ascending part and a horizontal part 20 on its profile adapted to interact with the lower end of the plunger 4. A third guide member 21 having an ascending profile to act upon said lower end of the plunger 4 for its further movement upwards within the receptacle 1 to remove the coal sample therefrom is placed along the receptacle path of rotation in series with the second guide member 19. Farther on, in series with the third guide member 21 and also along the receptacle path of rotation but on a circle with a radius somewhat greater then the distance between the axis of the shaft 3 and the outward generating line of the plunger 4, there is positioned a fourth guide member 22 with a descending profile. The latter acts through the pin 5 on the plunger 4 so as to bring it to the lower-most position. The guide members 21 and 22 are rigidly secured to the casing 7. The guide member 19 has one end thereof fixed to a shaft 23 which extends outside through suitable seals in the casing 7, the other end thereof bearing up against a shoulder 24 on the guide member 21. The shaft 23 is rotatable in suitable bearings (not shown). The outside end of the shaft 23 carries a lever 25 (or a system of levers) with a weight 26 which creates a specified pressure exerted on a coal sample in the receptacle 1 as this comes onto the horizontal part 20 of the guide member 19. The latter, through said lever 25, is also connected with a means for indicating the beginning of a displacement thereof together with the plunger 4 caused by the coal-sample swelling. To effect the indicating function the lever 25 is provided with a just 27 against which the short arm of a lever comprising a primary element 29 is permanently pressed under the action of a spring 28, shown in FIG. 2. The lever is rotatably mounted on a pin 30. The end of the other arm of the primary element 29 has a control element 31 adjustably mounted thereof (e.g. with the aid of a slot and clamp), so that the latter can be shifted relative to said primary element 29 in the direction of its turning. When the primary element 29 is turned, the control element 31 acts upon an electric sensor 32 which is connected to the electrical control circuit of the motor 16 (see FIG. 1) and is used for actuating this motor at the beginning of the coal-sample swelling. The sensor 32 is mounted on a secondary element 33 (FIG. 2) of said indicating means, which element is a lever made integral with a brake disc 34 and rotatable on the pin 30 as well as the primary element 29. Urged by the section of a spring 35, the secondary element 33 tends to turn with respect to the primary element 19 so that the sensor 32 moves away from the control element 31, but is blocked by means of a stop pin 36 fastened to the brake disc 34 which bears up against a stud 37 projecting from the primary element 29.

Figure 2:
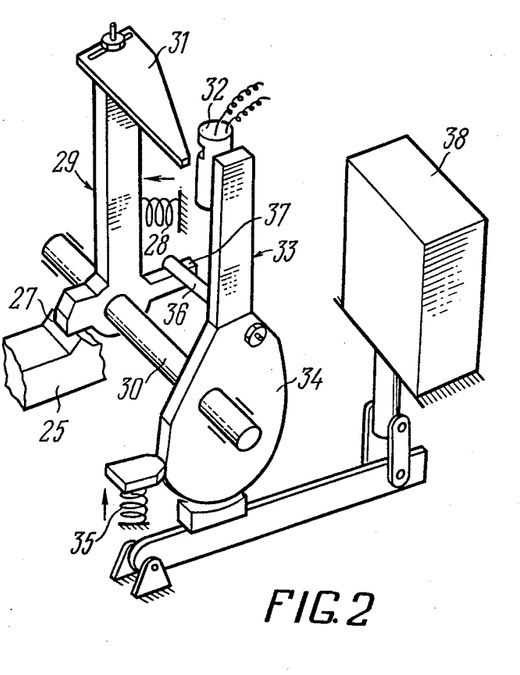
FIG. 2 is a kinematic diagram of said indicating means according to the invention.

The brake disc 34 is controlled by a solenoid 38 which, upon energization, fixes the secondary element 33 in position, whereby the primary elements 29 and the secondary element 33 become disengaged on signal from a sensor 39 (see FIG. 1) connected to the control circuit of the motor 16 for stopping rotation of the shaft 3 as the receptacle 1 and the plunger 4 pass along the horizontal part 20 of the second guide member 19. The sensor 39 is actuated by the control element 17, and so is a sensor 40 which is also connected to the control circuit of the motor 16 for stopping rotation of the shaft 3 as the receptacle 1 comes to a position preceding the intersection of its path of rotation with a stream of coal.

The guide member 18 is adapted to shift from the level of the top end face of the receptacle 1. To this end, the guide member 18 is rigidly mounted on the end of an axle 41 rotatable in bearings (not shown), part of this axle extending outside the casing 7 through a suitable seal in the wall thereof. Rigidly mounted on this part of the axle 41 outside the casing 7 is a lever 42 which is pressed against a dead stop 43 by means of a locking device 44, e.g. a screw with a self-locking thread, which abuts the lever 42 and is either turned by hand or power-driven through remote control. This screw forms a controlled lock for fixing the guide member 18 in alignment with the top end face of the receptacle 1.

The control circuit of the apparatus is provided with a time relay (not shown in the drawings) which is actuated at the starting thereof.

The time relay is preset to provide a time lag which is somewhat longer than the normal working cycle of the apparatus.

In the event the working cycle is not completed during this timing-out and the apparatus is not stopped in the initial position by the sensor 40, the time relay will disable the motor 16, actuate the brake 15 and generate a signal indicative of an emergency situation for the operator to take a corrective action. This adds up to operational reliability of the apparatus.

The apparatus according to the invention operates in the following manner.

Figure 3:
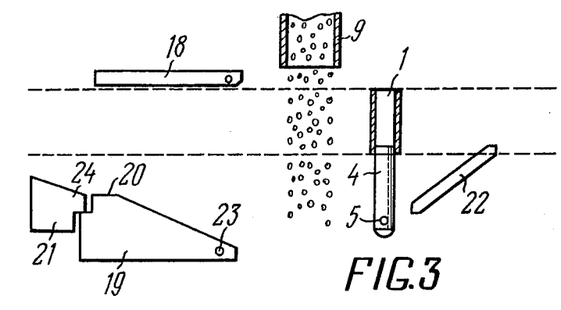
FIGS. 3–6 illustrate diagrammatically the movement of the receptacle with the plunger from the initial position thereof to the position where the coal sample in the receptacle is put under pressure.

Prior to the beginning of a working cycle, the bracket 2 with the receptacle 1 and the plunger 4 is in the initial position, i.e. next to the coal feed pipe 9 (see FIGS 1, 3) through which passes a stream of heated coal.

By depressing a push-button switch "Start" (not shown) at the central control station, the operator originates an electric signal to start the electric motor 16, disable the brake 15, and energize the time relay.

Where an installation incorporating the apparatus operates automatically, such a signal can be generated by a program control unit monitoring the working cycle of the installation.

The starting signal having been received, the working cycle proceeds automatically.

The electric motor 16 through the reduction gear unit 14 and the bevel gearing 11 imparts rotation to the shaft 3 with the bracket 2, the receptacle 1 and the plunger 4.

Figure 4:
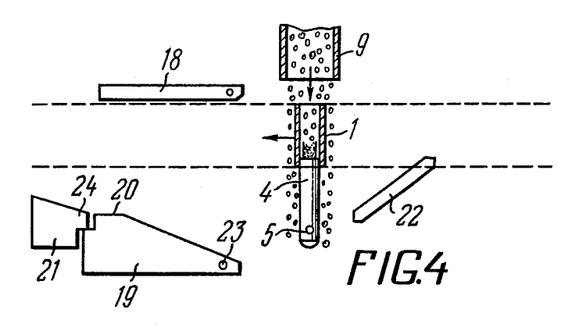
Figure 5:
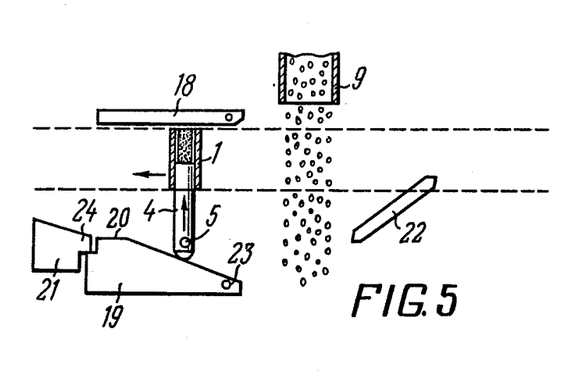

While moving, the receptacle 1 pass under the coal feed pipe 9 thereby intersecting a stream of heated coal, and takes some coal as a test sample, as illustrated in FIG. 4. Moving further on, the top end face of the receptacle 1 comes under the first guide member 18, which closes the passage thereof, as shown in FIG. 5.

Here, the edge of the guide member 18 removes excess coal from the top of the receptacle 1.

At the same time the plunger 4 by its lower end comes in contact with the second guide member 19 whereby, while moving further on, it is driven upwards to compress the coal sample in the receptacle 1.

Figure 6:
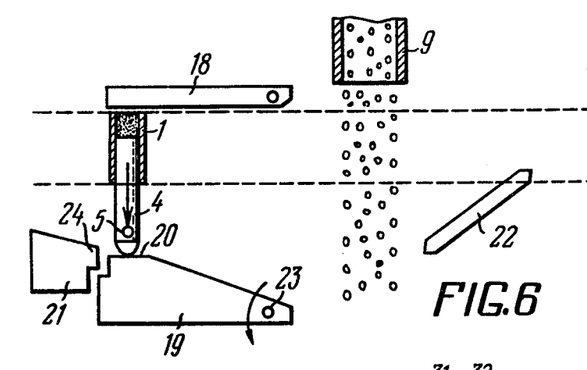
Figure 7:
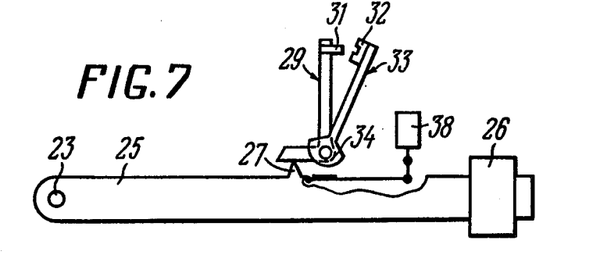
FIGS. 7, 8 illustrate diagrammatically possible positions of elements of said indicating means, according to the invention, prior to the beginning of the coal-sample swelling.
Figure 8:
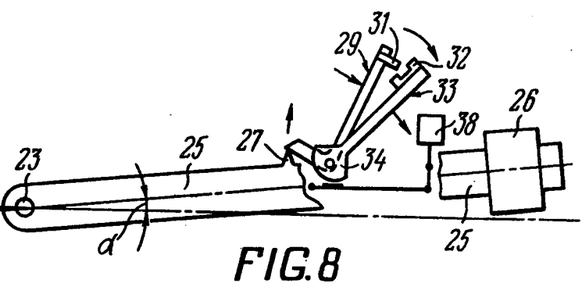

With adequately heat-treated coal, the sample thereof becomes compressed to a volume at which the plunger 4 coming onto a horizontal part 20 (FIG. 6) of the second guide member 19 either does not displace this guide member and the lever 25 (FIG. 7) downwards at all, or displaces these through a small angle α, as shown in FIG. 8. The lever 25 acts on the primary element 29 so that the latter turns on the pin 30 along with the secondary element 33 and the sensor 32. As the plunger 4 comes onto the horizontal portion 20 (FIG. 6) of the second guide member profile, the control element 17, shown in FIG. 1, actuates the sensor 39. That causes the stoppage of the motor 16, the braking action of the brake 15 and of the solenoid 38 (see FIG. 8), and a signal applied to an electric timer at the central control station (not shown).

The coal sample in the receptacle 1 is kept under a specified pressure created by the weight 26, until it begins swelling.

Figure 9:
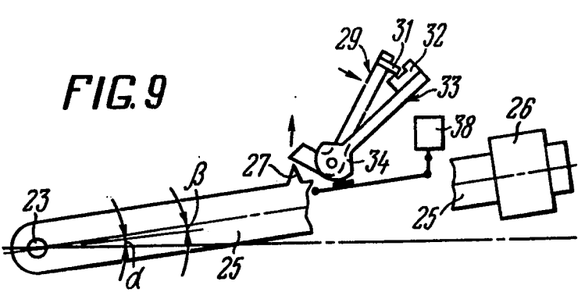
FIG. 9 illustrates diagrammatically a position of said indicating means, according to the invention, at the beginning of the coal-sample swelling.

The swelling of the coal in the receptacle 1 causes a certain displacement of the plunger 4 downwards, and the plunger turns the guide member 19, the lever 25 and the primary element 29 additionally through an angle β, as shown in FIG. 9. The primary element 29 turning under the action of the jut 27 on the lever 25 becomes disengaged from the secondary element 33 which has been locked in position by braking through the action of the solenoid 38. Therefore, the primary element 29 moves relative to the secondary element 33 and the control element 31 acts on the sensor 32.

The operation of the sensor 32 actuates the motor 16, interrupts the braking action of the brake 15 and the solenoid 38, and stops the electric timer.

The timer reading, i.e. the time span between the moment when the specified pressure is exerted on the coal sample in the receptacle 1 and the beginning of the coal swelling characterizes, as mentioned hereinbefore, the readiness of the heat-treated coal for moulding.

Figure 10:
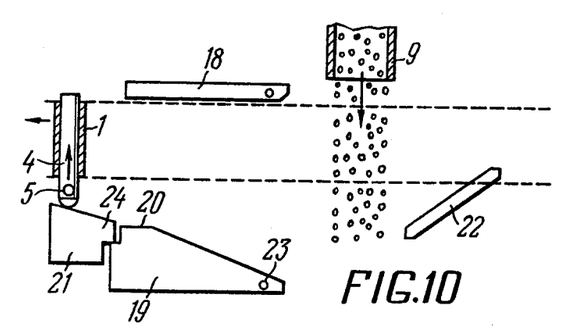
FIGS. 10, 11 illustrates diagrammatically the movement of the receptacle with the plunger after the completion of testing and prior to their return to the initial position.
Figure 11:
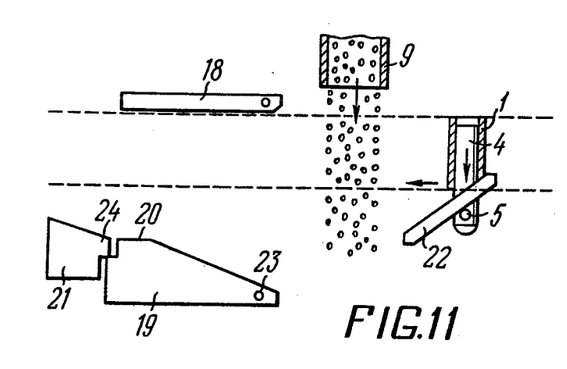

As the receptacle 1 moves further on along its circular path, its top end comes out of contact with the first guide member 18 (see FIG. 1 and 10), the plunger 4 by its lower end comes into contact with the third guide member 21 which drives it upwards in the receptacle 1 so that the plunger pushes out the coal sample therefrom. The tested coal falls down onto the bottom of the casing 7 and through the disposal pipe 10 (FIG. 1) is carried away with the coal stream. As it moves further along the path of rotation, the plunger 4 comes out of contact with the guide member 21, and its pin 5 engages the fourth guide member 22 (FIG. 11) which forces the plunger down until it comes to rest on the yoke 6 (FIG. 1).

When the bracket 2 comes to its initial position, the working cycle is over, the control element 17 acts on the sensor 40 whereby the apparatus is stopped until the next cycle.

With poorly heat-treated coal, the coal sample in the receptacle 1 permits only some initial packing but does not lend itself to a further compression by the weight 26. As a result, the resistance to further rotation of the shaft 3 mounts and so does the torque on the shaft 12. When this torque reaches the maximum permissible value for which the safety clutch 13 has been set up, the latter beings to slip, with the shafts 3 and 12 brought to a stand-still.

The clutch 13 goeas on slipping until the predetermined delay period, for which the time relay has been set up, runs out whereupon the time relay develops a command signal to stop the motor 16, to actuate the brake 15, and to produce an emergency signal for the operator.

Having received the emergency signal, the operator withdraws the locking device 44, which makes it possible for the guide member 18 to turn upwards, and, by reiterated actuation of the motor 16, brings the receptacle 1 to the initial position, simultaneously emptying it of the coal sample.

What is claimed is:

1. An apparatus for testing the readiness of heat-treated coal for moulding, said readiness being assessed in terms of time as a span between the moment of exerting pressure on a sample of heated coal and the beginning of the coal-sample swelling, comprising: a casing, a vertical shaft placed in said casing and having an end extending outside the casing; a drive connected to said end of the shaft; a bracket placed in the casing and fixed by one of its end on said shaft; a receptacle for accommodating a coal sample, said receptacle being a sleeve open at both ends, fixed vertically on the other end of said bracket; a feed pipe for letting a stream of coal in the casing, said pipe being positioned on the top thereof over the path of rotation of the receptacle with the shaft; a slanted bottom of said casing; a disposal pipe for removing the coal from the casing, said pipe being located on the slanted bottom thereof; a plunger adapted to enter said receptacle and move therethrough; means for moving said plunger in said receptacle during rotation thereof with the shaft to compress the coal sample therein, said means having a first guide member, positioned in said casing along the path of rotation of the receptacle with the plunger so as to be in a horizontal plane at the level of the top end face of the receptacle and to close the entrance passage thereof on the corresponding portion of said path of rotation, said means having a second guide member, placed in said casing on the same portion of the receptacle path of rotation under the first guide member; a weight; a lever system which kinematically connects said second guide member with said weight whereby the second guide member is urged towards the first guide member; said second guide member having an ascending and horizontal parts of the profile of said second guide member used for interaction with the lower end of said plunger as it rotates with the receptacle, whereby the plunger is driven upwards and the coal sample is compressed in the receptacle between the plunger and said first guide member; said means having a third guide member, fixedly positioned in the casing along the subsequent portion of the receptacle path of rotation and having an ascending profile used for interaction with the plunger to cause a further upward movement thereof in the receptacle for the removal of the coal sample therefrom; said means having a fourth guide member fixedly positioned in the casing along the receptacle path of rotation in series with the third guide member and having a descending profile used to interact with said plunger for bringing it into its lowermost position; a means for indicating the beginning of a displacement of the plunger with said second guide member caused by the coal-sample swelling, said indicating means being kinematically connected with said second guide member through said lever system; means for stopping said drive of the shaft rotation when the receptacle comes to a position preceding the intersection of its path of rotation and the stream of coal, and to a position on the horizontal part of the profile of said second guide member; and a means for actuating said drive of the shaft rotation when the coal sample begins swelling.

2. An apparatus as claimed in claim 1, comprising: a primary element of said means for indicating the beginning of the plunger displacement caused by the coal-sample swelling, said element being kinematically connected with said lever system; a secondary element of said indicating means adapted to be brought in engagement with said primary element; means for disengaging said secondary element from said primary element on a single generated by said means for stopping said drive when the receptacle with the plunger comes onto the horizontal part of the profile of said second guide member a sensor for generating a signal indicative of the beginning of the coal-sample swelling, said sensor being attached to said secondary element and operating as said primary element is displaced relative thereto.

3. An apparatus as claimed in claim 1, comprising: a safety clutch incorporated in said drive of the shaft, said cluth slipping when the receptacle and the plunger get jammed between said first and second guide members while compressing a sample of poorly heated coal; said first guide member adapted to be displaced from the lever of the top end face of said receptacle; a controllable locking device for fixing said first guide member at the lever of the top end face of said receptacle.

4. An apparatus as claimed in claim 2, comprising: a safety clutch incorporated in said drive of the shaft, said clutch slipping when the receptacle and the plunger get jammed between said first and second guide members while compressing a sample of poorly heated coal; said first guide member adapted to be displaced from the level of the top end face of said receptacle; a controllable locking device for fixing said first guide member at the level of the top end face of said receptacle.

* * * * *